United States Patent [19]
Brummond et al.

[11] Patent Number: 5,543,311
[45] Date of Patent: Aug. 6, 1996

[54] LABELED CARBAMAZEPINE HAPTEN ANALOGUES FOR COMPETITIVE ENZYME IMMUNOASSAYS

[75] Inventors: Barbara A. Brummond, Rochester; Mohan S. Saini; Ignazio S. Ponticello, both of Pittsford, all of N.Y.

[73] Assignee: Johnson & Johnson Clinical Diagnostics, Inc., Rochester, N.Y.

[21] Appl. No.: 926,203

[22] Filed: Aug. 7, 1992

[51] Int. Cl.$^6$ ........................ C12N 9/96
[52] U.S. Cl. .................... 435/188; 435/7.93
[58] Field of Search .................. 435/188, 7.93

[56] References Cited

U.S. PATENT DOCUMENTS

| | | | |
|---|---|---|---|
| 4,058,511 | 11/1977 | Singh | 436/543 |
| 4,404,366 | 9/1983 | Boguslaski et al. | 536/5 |
| 4,442,204 | 4/1984 | Greenquist et al. | 435/7.7 |
| 4,476,229 | 10/1984 | Fino et al. | 436/537 |
| 4,559,173 | 12/1985 | Flentge | 540/542 |
| 4,593,089 | 6/1986 | Wang et al. | 436/536 |
| 4,952,691 | 8/1990 | Wang et al. | 544/300 |

FOREIGN PATENT DOCUMENTS

| | | |
|---|---|---|
| 56187559 | 12/1979 | Japan . |
| 571109724 | 12/1980 | Japan . |

OTHER PUBLICATIONS

A. Sidki et al., Clin. Chem., vol. 30/8, 1348–1352 (1984).
T. Li et al., Epilepsia, vol. 23, 391–398 (1982).
J. Paxton et al., J. Pharmacol. Methods, vol. 3, 289–296 (1980).

*Primary Examiner*—Mary E. Ceperley
*Attorney, Agent, or Firm*—John W. Wallen, III

[57] ABSTRACT

A labeled carbamazepine analogue is described comprising:

(A) a label, of the type used in immunoassays, having an amine or sulfhydryl group such as horseradish peroxidase;

(B) a carbamazepine nucleus; and (C) a linking chain linking the carboxamide group of the carbamazepine nucleus to the label, said linking chain having about 4 to about 40 atoms consisting of:

(1) $C_2$ to $C_6$ alkylene groups; and (2) 5 to 7 membered heterocyclic ring groups, each group being joined into the linking group through chemical groups selected from (a) esters,
(b) amides
(c) heteroatoms selected from —O—, —S—, and —NR—; wherein R represents hydrogen or $C_1$ to $C_6$ alkyl; and
(d) carbonyl.

The new labeled analogues are useful in immunoassay elements and processes for detection of carbamazepine drugs, for example, in body fluids.

7 Claims, No Drawings

LABELED CARBAMAZEPINE HAPTEN ANALOGUES FOR COMPETITIVE ENZYME IMMUNOASSAYS

RELATED CASES

Novel Carbamazepine Hapten Analogues by Ponticello and Saini U.S. patent application Ser. No. 926,205, now U.S. Pat. No. 5,395,933, filed on even date herewith and Immunoassays With Novel Labeled Carbamazepine Hapten Analogues by Brummond, Saini, and Ponticello, U.S. patent application Ser. No. 926,202 also filed on even date herewith.

FIELD OF THE INVENTION

This invention relates to clinical chemistry, particularly immunoassays.

BACKGROUND OF THE INVENTION

Immunoassays, which take advantage of natural immunological reactions, have found wide-spread use as analytical techniques in clinical chemistry. Because of the specificity of the reactions, they are particularly advantageous in quantifying biological analytes that are present in very low concentration in biological fluids. Such analytes (called ligands herein) include, for example, antibodies, therapeutic drugs, narcotics, enzymes, hormones, proteins, etc.

In competitive binding immunoassays, a labeled ligand, including immunocompetent derivatives and analogs of the ligand, is placed in competition with unlabeled ligand for reaction with a fixed amount of the appropriate binding material (called a receptor herein). Unknown concentrations of the ligand can be determined from the measured signal of either the bound or unbound (i.e. free) labeled ligand. The reaction proceeds as follows:

ligand+labeled ligand+receptor→ligand-receptor+labeled ligand-receptor.

Conventional labels include radioactive tags, enzymes, chromophores, fluorophores, stable free radicals, and enzyme cofactors, coenzymes, inhibitors and allosteric effectors.

Consistent with the foregoing an immunoassay for ligands such as carbamazepine in serum can be based on competition between (1) an enzyme labeled carbamazepine analogue (sometimes referred to hereafter as LDH) with (2) the carbamazepine in a patients blood serum for immobilized antibody binding sites.

Specific requirements for the LDH include: 1) at least about 70–90% of the LDH can be bound by excess immobilized carbamazepine antibodies; 2) affinity of the LDH for immobilized antibodies is such that competition of a fixed amount of carbamazepine occurs in a therapeutically relevant concentration range; and 3) stability of the LDH against hydrolysis of its enzyme label under storage conditions. Requirements imposed on the carbamazepine hapten analogue include: 1) accessibility of the derivative to the immobilized antibody following conjugation with the enzyme label; 2) specific recognition of the derivative by the antibody to the carbamazepine; 3) sufficient reactivity of the derivative with the enzyme label, either directly or following activation of the enzyme or derivative, under conditions that do not adversely affect enzyme activity; 4) stability of the label against hydrolysis of the carbamazepine hapten from the enzyme; and 5) fast and complete attachment of the carbamazepine hapten to the enzyme by covalent bonding, without denaturing the enzyme.

STATEMENT OF THE INVENTION

The present invention provides a labeled carbamazepine analogue comprising:

(A) a label, of the type used in immunoassays, having an amine or sulfhydryl group;

(B) a carbamazepine nucleus; and (C) a linking chain linking the carboxamide group of the carbamazepine nucleus to the label group through a carbonyl group, the linking chain having about 4 to about 40 atoms consisting of:

(1) $C_2$ to $C_6$ alkylene groups; and (2) 5 to 7 membered heterocyclic ring groups selected from 1,4-piperazinylene; 2,5-dimethyl-1,4-piperazinylene; 1,3-imidazolidinylene, and 1,4-hexahydrodiazepinylene;

each group being joined into the linking group through chemical groups selected from (a) esters, including thioesters $$(-\overset{\overset{\displaystyle O}{\|}}{C}Z-),$$

where Z is O or S;

(b) amides, $$(-\overset{\overset{\displaystyle O}{\|}}{C}NR-),$$

wherein R represents hydrogen or $C_1$ to $C_6$ alkyl (c) hetero atoms selected from —O—, —S—, and —NR—; wherein R represents hydrogen or $C_1$ to $C_6$ alkyl; and (d) carbonyl.

The labeled drug hapten analogues defined above include those conforming to the structure (I):

Structure I $$\text{[carbamazepine nucleus]}-N-\left[\overset{O}{\underset{\|}{C}}-\overset{R}{\underset{|}{N}}-R^2\right]_l-\left[\overset{O}{\underset{\|}{C}}-N\underset{R^7}{\overset{R^1}{\diagdown\diagup}}N-\overset{O}{\underset{\|}{C}}-R^3\right]_m$$

$$-\left[\overset{O}{\underset{\|}{C}}-Z-R^4-Z-\overset{O}{\underset{\|}{C}}-R^5\right]_n-\overset{O}{\underset{\|}{C}}-\text{LABEL}$$

wherein

R represents hydrogen or lower alkyl of about 1 to 6 carbon atoms $R^1$ is alkylene of 1 to 3 carbon atoms sufficient to form with $R^7$ a heterocylic group selected from 1,4-piperazinylene; 2,5-dimethyl-1,4-piperazinylene; 1,3-imidazolidinylene, and 1,4-hexahydrodiazepinylene;

$R^2$, $R^3$, $R^4$, and $R^5$, each independently represent alkylene groups of about 2 to 10 carbon atoms and phenylene;

$R^7$ is hydrogen or methyl;

each Z independently represents —O—, —S—, or —NR— wherein R represents hydrogen or lower alkyl of about 1 to 6 carbon atoms:

LABEL is an enzyme l is 0, 1 or 2;

m is 0, 1, or 2;

n is 0, 1, or 2; and (i) the sum of carbon and hetero atoms in the linear chain comprising $R^2$, $R^3$, $R^4$, and $R^5$ and the linking atoms which join them is about 5 to 40, (ii) provided that the bracketed components of structure I can appear therein in any order; and (iii) only one of $R^2$, $R^3$, $R^4$, and $R^5$ can be phenylene.

The labeled hapten drug analogues, such as carbamazepine, having short linking chains between the carbamazepine nucleus and labels, such as horseradish peroxidase (HRP) were acceptable for use with some immobilized antibodies. Hapten analogues with a longer linking group between the Label and the carbamazepine nucleus were strongly bound by the immobilized antibodies tested. Linking groups having amide bonds instead of ester bonds are resistant to hydrolysis and therefore avoids any problem of separation of the label hapten nucleus from the label. The carbamazepine-HRP labels of this invention with extended linkers have the ability to be completely bound (>90%) by most of the immobilized antibody types we have prepared. This allows us to pursue a variety of antibodies to develop the carbamazepine enzyme immunoassay.

DETAILS OF THE INVENTION

We have devised a new method for the preparation of labeled carbamazepine drug hapten analogues. The label has an amine or sulfhydryl group through which it is covalently bound through a linking group to a hapten. The label can include visible dyes, fluorescent dyes, enzymes, and radioactive labels. An especially useful enzyme label is horseradish peroxidase (HRP), especially amine enriched horseradish peroxidase.

The new method comprises the steps of:

1) contacting (A) a label having an amine or sulfhydryl group thereon, with an excess of a (B) carbamazepine analogue comprising:
  (i) an active ester group such as succinimidoxycarbonyl;
  (ii) a carbamazepine nucleus; and
  (iii) a linking chain (i) linking the carboxamide group of the carbamazepine nucleus to the active ester group through a carbonyl group (The linking group is otherwise identical to the linking group defined previously herein); and 2) removing the unused 5H-dibenzo[b,f]azepine-5-carboxamide drug hapten analogue and condensation by-products, preferably by dialysis.

Preferably the step of contacting is carried out by dissolving both the 5H-dibenzo[b,f]azepine-5-carboxamide drug hapten analogue, such as carbamazepine, and the label in a water-miscible organic solvent such as N,N-dimethylformamide or dimethyl sulfoxide or a mixture of solvent and water (buffered) before mixing together.

All the labeled carbamazepine analogues prepared by the above method are new chemical compositions of matter.

The preparation of the intermediate carbamazepine analogues, from which the labeled counterparts are made are prepared as described below.

PREPARATORY EXAMPLE 1

N-[2-(3-Succinimidoxycarbonylpropionyloxy)ethyl]carbamazepine

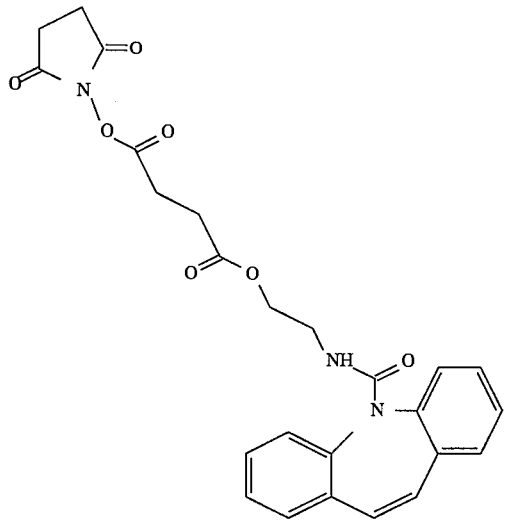

Step 1: Preparation of N-(2-Hydroxyethyl)carbamazepine

A mixture of ethanolamine (6.1 g, 0.1 mole) and 5-chlorocarbonyl-2,2'-iminostilbene (6.5 g, 0.025 mole) in toluene (250 mL) was heated at reflux for 4 hours and then allowed to stand at ambient temperature for 16 hours. To the mixture was added dichloromethane (500 mL), and the solution was washed with 10% hydrochloric acid (2×100 mL), washed with saturated sodium bicarbonate solution (100 mL), washed with saturated sodium chloride solution (100 mL), dried over anhydrous magnesium sulfate, filtered, and the solvent removed on a rotary evaporator.

To the residue was added dichloromethane (45 mL) and ethyl acetate (75 mL), and the mixture was placed in the freezer (−16° C.). The solid was filtered.

Step 2: N-[2-(3-Carboxypropionyloxy)ethyl]carbamazepine

A mixture of N-(2-hydroxyethyl)carbamazepine (5.6 g, 0.02 mole), succinic anhydride (2.2 g, 0.02 mole), and dimethylaminopyridine (2.4 g, 0.02 mole) in chloroform (25 mL) was stirred at ambient temperature for 24 hours. Dichloromethane (400 mL) was added, and the mixture was washed with 10% hydrochloric acid solution (2×100 mL), washed with saturated sodium chloride solution (100 mL), dried over anhydrous magnesium sulfate, filtered, and the solvent removed. To the residue was added ethyl ether (25 mL) and petroleum ether (25 mL). A sample was recrystallized from methanol.

Step 3: N-[2-(3-Succinimidoxycarbonylpropionyloxy)ethyl]carbamazepine

A mixture of N-[2-(3-carboxypropionyloxy)ethyl]carbamazepine (3.8 g, 0.01 mole), N,N'-dicyclohexylcarbodiimide (2.1 g, 0.01 mole), and N-hydroxysuccinimide (1.2 g, 0.01 mole) in chloroform (75 mL) was stirred at room temperature for 20 hours. The mixture was filtered, and the filtrate was concentrated on a rotary evaporator in vacuo to give a white solid. Analytical calculated for $C_{25}H_{23}N_3O_7$: C, 62.89; H, 4.86;N, 8.80. Found C, 60.74: H, 5.12. N, 8.83.

PREPARATORY EXAMPLE 2

N-[3-(3-Succinimidoxycarbonylpropionamido)propyl]carbamazepine

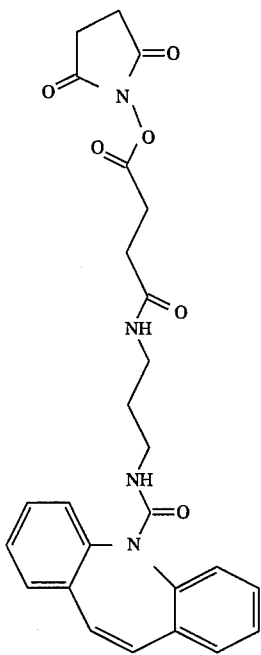

Step 1: N-[3-(Benzyloxycarbonylamino)propyl]carbamazepine

A mixture of N-benzyloxycarbonyl-1,3-propanediamine (8.0 g, 0.04 mole) and triethylamine (5.0 g, 0.05 mole) in chloroform (75 mL) was added dropwise over 15 minutes to 5-chlorocarbonyl-2,2'-iminostilbene (7.6 g, 0.03 mole) in chloroform (200 mL). The mixture was then heated at reflux for 1 hour and at ambient temperature for 16 hours. Dichloromethane (500 mL) was added, and the mixture was washed with 10% hydrochloric acid (2×100 mL), washed with saturated sodium chloride solution (100 mL), dried over anhydrous magnesium sulfate, filtered, and the solvent removed on a rotary evaporator in vacuo. To the residue was added ethyl acetate (50 mL) and the solution placed in the freezer for 2 hours and filtered.

Step 2: N-(3-Aminopropyl)carbamazepine Hydrobromide

N-[3-(Benzyloxycarbonylamino)propyl]carbamazepine (13.2 g, 0.03 mole) and 30–35% hydrogen bromide-acetic acid solution (70 mL) was allowed to stir at room temperature for 1 hour. This mixture was then poured into diethyl ether (3 L), and the solid which forms was triturated with fresh portions of ether (3×1 L). The solid was filtered.

Step 3: N-[3-(3-Carboxypropionamido)propyl]carbamazepine

A mixture of N-(3-aminopropyl)carbamazepine hydrobromide (7.5 g, 0.02 mole), triethylamine (2.0 g, 0.02 mole), and succinic anhydride (2.0 g, 0.02 mole) in chloroform 1200 mL) was heated for 30 minutes at 50°–60° C. and allowed to stand at ambient temperature for 20 hours. Dichloromethane (500 mL) was added, and the mixture was washed with 10% hydrochloric acid (2×100 mL) and saturated sodium chloride solution (100 mL), then dried over anhydrous magnesium sulfate, filtered, and the solvent removed on a rotary evaporator in vacuo. To the residue was added dichloromethane (100 mL) and petroleum ether (100 mL), and it was placed in the freezer overnight. The solid was filtered.

Step 4: N-[3-(3-Succinimidoxycarbonylpropionamido)propyl]carbamazepine

A mixture of N-[3-(3-carboxypropionamido)propyl]carbamazepine (3.3 g, 0.01 mole), N,N'-dicyclohexylcarbodiimide (2.0 g, 0.01 mole), and N-hydroxysuccinimide (1.0 g, 0.01 mole) in chloroform (80 mL) was stirred at room temperature for 20 hours. The mixture was filtered and the solvent removed on a rotary evaporator in vacuo to give 4.7 g. The solid was dissolved in dichloromethane (20 mL), filtered and the solvent removed. This procedure was repeated an additional time to give 3.0 g (64% yield). Analytical calculated for $C_{26}H_{26}N_3O_6$: C, 65.54; H, 5.50; N, 8.82. Found: C, 62,38; H, 5.47; N, 11.02.

PREPARATORY EXAMPLE 3

N-[3-(4-Succinimidoxycarbonylbutyramido)propyl]carbamazepine

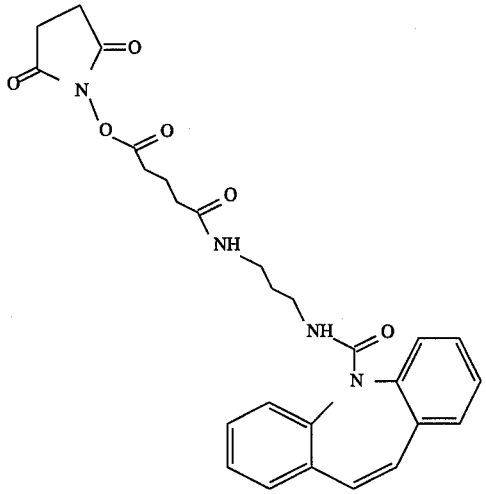

Step 1: N-[3-(4-Carboxybutyramido)propyl]carbamazepine

N-(3-aminopropyl)carbamazepine hydrobromide (4.8 g, 0.0128 mole) was treated with glutaric anhydride (1.5 g, 0.0128 mole), triethylamine (1.4 g, 0.014 mole) by the procedures described in step 3 of Preparatory Example 2.

Step 2: N-[3-(4-Succinimidoxycarbonylbutyramido)propyl]carbamazepine

N-[3-(4-Carboxybutyramido)propyl]carbamazepine was treated with N-hydroxysuccinimide by the procedure described in step 4 of Preparatory Example 2 to give the product. Analytical calculated for $C_{27}H_{28}N_4O_6$: C, 64.28; H, 5.59; N, 11.10. Found: C, 63.84; H, 5.72; N, 10.89.

PREPARATORY EXAMPLE 4

N-[6-(4-Succinimidoxycarbonylbutyramido)hexyl]carbamazepine

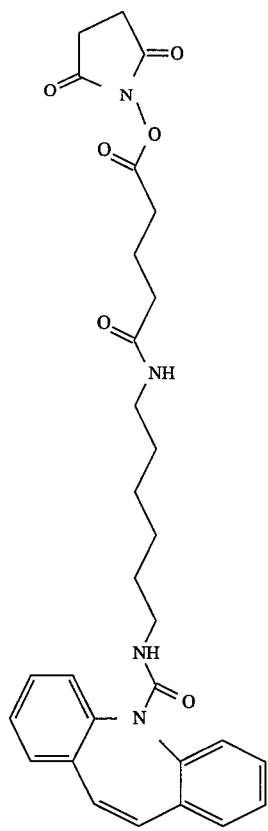

Step 1: N-[6-(Benzyloxycarbonylamino)hexyl]carbamazepine

This material was prepared using the procedure outlined in step 1, Preparatory Example 2, except using N-benzyloxycarbonyl-1,6-hexanediamine in place of the N-benzyloxycarbonyl-1,3-propanediamine, to give 11.0 g (94% yield). Pure material was obtained by crystallization from ethyl acetate/pentane (1:1).

Step 2: N-(6-Aminohexyl)carbamazepine Hydrobromide

This material was prepared using the procedure outlined in Preparatory Example 2, step 2, except substituting N-[6-(benzyloxycarbonylamino)hexyl]carbamazepine for the N-[3-benzyloxycarbonylamino)propyl]carbamazepine, to give 8.5 g (100% yield).

Step 3: N-[6-(4-Carboxybutyramido)hexyl]carbamazepine

This material was prepared using the procedure outlined in step 3, Preparatory Example 2, except substituting N-(6-aminohexyl)carbamazepine hydrobromide and glutaric anhydride, respectively, for the N-(3-aminopropyl)carbamazepine hydrobromide and succinic anhydride. The product was crystallized from dichloromethane/ethyl acetate (1:1).

Step 4: N-[6-(4-Succinimidoxycarbonylbutyramido)hexyl]carbamazepine

This material was prepared using the procedure outlined in Preparatory Example 2, step 4, except substituting N-[6-(4-carboxybutyramido)hexyl]carbamazepine for the N-[3-(3-carboxypropionamido)propyl]carbamazepine. Analytical calculated for $C_{30}H_{34}N_4O_6$: C, 65.92; H, 6.27; N, 10.25. Found: C, 65.20; H, 6.19; N, 10.02.

PREPARATORY EXAMPLE 5

5-[4-(4-Succinimidoxycarbonylbutyryl)piperazinocarbonyl]-5H-dibenzo[b,f]azepine

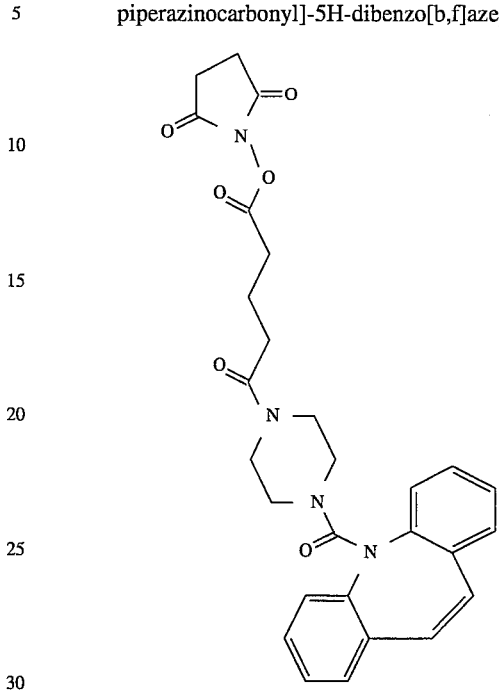

Step 1: 5-[4-(Benzyloxycarbonyl)piperazinocarbonyl]-5H-dibenzo[b,f]azepine

This material was prepared using the procedures outlined in Preparatory Example 2, step 1, except substituting benzyl 1-piperazinecarboxylate in place of the N-benzyloxycarbonyl-1,3-propanediamine.

The compound was dissolved in ethyl ether (10 mL) and petroleum ether was added to the cloud point. The mixture was placed in a freezer, and then filtered to give 9.3 g material.

Step 2A: 5-(Piperazinocarbonyl)-5H-dibenzo[b,f]azepine Hydrobromide

Step 2B: 5-[4-(4-Carboxybutyryl)piperazinocarbonyl]-5H-dibenzo[b,f]azepine

These materials were prepared using the procedures outlined in Steps 2 and 3 of Preparatory Example 2, except starting with 5-[4-(benzyloxycarbonyl)piperazinocarbonyl]-5H-dibenzo[b,f]azepine in place of the N-[3-(benzyloxycarbonylamino)propyl]carbamazepine in step 2, and thus the product 5-(Piperazinocarbonyl)-5 H-dibenzo-[b,f]azepine Hydrobromide in place of the product of step 2, and glutaric anhydride in place of succinic anhydride in the procedures of step 3. The residue (2B) was crystallized from ethyl acetate (10 mL) and petroleum ether (2 mL), placed in a freezer, and filtered to give the acid.

Step 3: 5-[4-(3-Carboxypropionyl)piperazinocarbonyl]-5H-dibenzo[b,f]azepine

This material was prepared using the procedures outlined in step 2B of Preparatory Example 4, except using succinic anhydride in place of glutaric anhydride. A sample recrystallized from dichloromethane/ethyl acetate (1:1) gave pure material.

Step 4: 5-[4-(4-Succinimidoxycarbonylbutyryl)piperazinocarbonyl]-5H-dibenzo[b,f]azepine This material was prepared using the procedure outlined in Preparatory Example 2, step 4, except using 5-[4-(carboxybutyryl)piperazinocarbonyl]-5H-dibenzo[b,f]azepine in place of the N-[3-(3-carboxypropionamido)propyl]carbamazepine to give 4.6 g (100% yield). The material (3.0 g) was chromatographed using silica gel. Analytical calculated for $C_{28}H_{28}N_4O_6$: C, 65.09; H, 5.47; N, 10.85. Found: C, 64.87; H, 5.99; N, 10.62.

PREPARATORY EXAMPLE 6

5-[4-(3-Succinimidoxycarbonylpropionyl)piperazinocarbonyl]-5H-dibenzo[b,f]azepine

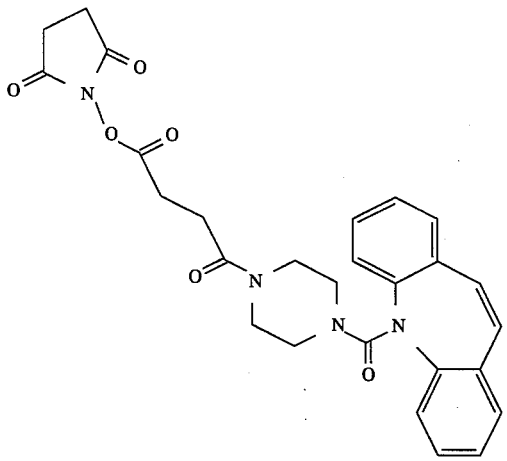

This material was prepared using the procedure outlined in step 4, Preparatory Example 2, except using 5-[4-(3-carboxypropionyl)piperazinocarbonyl]-5H-dibenzo[b,f]azepine in place of the N-[3-(3-carboxypropionamido)propyl]carbamazepine. A sample was recrystallized from dichloromethane (35 mL) and ethyl acetate (8 mL) to give material melting at 135°–140° C. Analytical calculated for $C_{27}H_{26}N_4O_6$: C, 64.33; H, 5.22; N, 11.15. Found: C, 62.46; H, 5.29; N, 10.82.

PREPARATORY EXAMPLE 7

N-(4-Succinimidoxycarbonylbutyl)carbamazepine

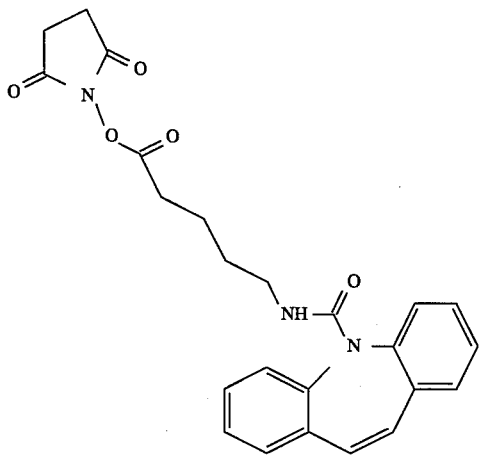

Step 1: N-(4-Methoxycarbonylbutyl)carbamazepine

To a mixture of sodium hydride (6.0 g, 0.2 mole, 80%) and carbamazepine (40.0 g, 0.17 mole) in tetrahydrofuran (400 mL) was added over 30 minutes methyl 5-bromovalerate (39.0 g, 0.19 mole) in tetrahydrofuran (100 mL). The mixture was stirred at ambient temperature for 3 days and then poured into ice containing concentrated hydrochloric acid (100 mL). The aqueous solution was extracted with dichloromethane (3×200 mL), and the combined organic solutions were washed with saturated sodium bicarbonate solution (200 mL), saturated sodium chloride solution (200 mL), then dried over anhydrous magnesium sulfate, filtered, and the solvent removed on a rotary evaporator in vacuo. To the residue was added ethyl ether (100 mL). The mixture was placed in the freezer (−16° C.) and filtered to give a white solid.

Step 2: N-(4-Carboxybutyl)carbamazepine

N-(4-Methoxycarbonylbutyl)carbamazepine (6.3 g, 0.18 mole) was dissolved in p-dioxane (120 mL), water (25 mL), and concentrated hydrochloric acid (50 mL). The solution was refluxed for 2 hours and then stirred to ambient temperature. To this mixture was added saturated sodium chloride solution (100 mL) and the mixture extracted with dichloromethane (3×300 mL). The combined organic solutions were washed with saturated sodium chloride solution (100 mL), dried over anhydrous magnesium sulfate, filtered, and the solvent removed. The residue was dissolved in dichloromethane (175 mL) and ethyl acetate (100 mL) was added. The mixture was placed in the freezer (−16° C.), and then filtered.

Step 3: N-(4-Succinimidoxycarbonylbutyl)carbamazepine

This material was prepared using the procedure outlined in Preparatory Example 2, step 4, except using N-(4-carboxybutyl)carbamazepine in place of the N-[3-(3-carboxypropionamido)propyl]carbamazepine. Analytical calculated for $C_{24}H_{23}N_3O_5$: C, 66.50; H, 5.35; N, 9.69. Found: C, 65.82; H, 5.58; N, 9.37.

PREPARATORY EXAMPLE 8

N-{4-[4-(3-Succinimidoxycarbonylpropionyl)piperazinocarbonyl]butyl}carbamazepine

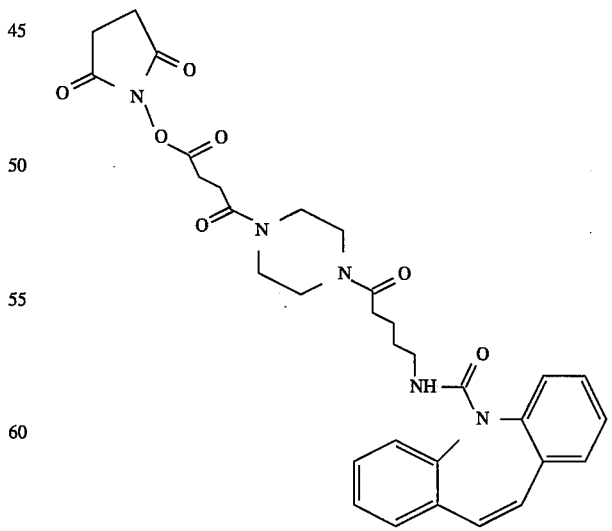

Step 1: N-[4-(4-Benzyloxycarbonylpiperazinocarbonyl)butyl]carbamazepine

A mixture of N-(4-carboxybutyl)carbamazepine (3.4 g, 0.01 mole) and 1,1'-carbonyldiimidazole (2.1 g, 0.0125 mole) in tetrahydrofuran (100 mL) was stirred at ambient temperature for 30 minutes. To this mixture was added at room temperature over 30 minutes benzyl 1-piperazinecarboxylate (2.75 g, 0.0125 mole) in tetrahydrofuran (100 mL). After 20 hours, dichloromethane (300 mL) was added, and the organic solution was washed with 5% hydrochloric acid solution (3×100 mL), washed with saturated sodium carbonate solution (100 mL), washed with saturated sodium chloride solution (100 mL), dried over anhydrous magnesium sulfate, filtered, and the solvent removed on a rotary evaporator in vacuo. The material was used directly in the next step.

Step 2A: N-(4-Piperazinocarbonylbutyl)carbamazepine Hydrobromide

Step 2B: N-{4-[4-(3-Carboxypropionyl)piperazinocarbonyl]butyl}carbamazepine

These materials were prepared using the procedures outlined in steps 2 and 3 of Preparatory Example 2, except starting with N-[4-(4-benzoyloxycarbonylpiperazinocarbonyl)butyl]carbamazepine in place of the N-[3-(benzoyloxycarbonylamino)propyl]carbamazepine in step 2A, and then using the product from step 2A of Preparatory Example 8 in place of the product of step 2 of Preparatory Example 2 in step 2B of Preparatory Example 8 to give the acid.

Step 3: N-{4-[4-(3-Succinimidoxycarbonylpropionyl)piperazinocarbonyl]butyl}carbamazepine This material was prepared using the procedure outlined in Example 2, step 4, except using N-{4-[4-(3-carboxypropionyl)piperazinocarbonyl]butyl}carbamazepine in place of the N-[3-(3-carboxypropionamido)propyl]carbamazepine. A sample was chromatographed using silica gel to give analytically pure material. Analytical calculated for $C_{32}H_{35}N_5O_7$: C, 63.88; H, 5.86; N, 11.64. Found: C, 63.13; H, 6.02; N, 11.06.

PREPARATORY EXAMPLE 9

N-{4-[3-(4-Succinimidoxycarbonylbutyramido)propylaminocarbonyl]butyl}carbamazepine Step 1: N-[4-(3-Benzyloxycarbonylaminopropylaminocarbonyl)butyl]carbamazepine This material was prepared using the procedure outlined in step 1 of Preparatory Example 8, except substituting N-benzyloxycarbonyl-1,3-propanediamine for the benzyl 1-piperazinocarboxylate. The residue was treated with ethyl ether (8 mL), acetone (4 mL), and petroleum ether (3 mL), placed in a freezer (−16° C.), and filtered to give the product.

Step 2A: N-[4-(3-Aminopropylaminocarbonyl)butyl]carbamazepine Hydrobromide

Step 2B: N-{4-[3-(4-Carboxybutyramido)propylaminocarbonyl]butyl}carbamazepine

These materials were prepared using the procedures outlined in steps 2 and 3 of Preparatory Example 2, except substituting N-[4-(3-benzyloxycarbonylaminopropylaminocarbonyl)butyl]carbamazepine in place of the N-[3-(benzyloxycarbonylamino)propyl] carbamazepine in step 2, and N-[4-(3-aminopropylaminocarbonyl)butyl]carbamazepine hydrobromide for the N-(3-aminopropyl)carbamazepine hydrobromide and glutaric anhydride for the succinic anhydride in step 3, to give 2.6 g (44%) yield. The solid was recrystallized from methanol (4 mL) and ethyl acetate (15 mL) to give pure material.

Step 3: N-{4-[3-(4-Succinimidoxycarbonylbutyramido)propylaminocarbonyl]butyl}carbamazepine This material was prepared using the procedures outlined in step 4 of Preparatory Example 2, except substituting N-{4-[3-(4-carboxybutyramido)propylaminocarbonyl]butyl}carbamazepine for the N-[3-( 3-carboxypropionamido)propyl]carbamazepine. A sample was chromatographed on silica gel to give a white solid. Analytical calculated for $C_{32}H_{37}N_5O_7$: C, 63.67; H, 6.18; N, 11.60. Found: C, 61.74; H, 6.21; N, 10.77.

UTILITY EXAMPLES

The following examples illustrate the preparation of the new labeled 5H-dibenzo[b,f]azepine- 5-carboxamide drug hapten analogue conjugates of this invention and their use.

Example 1

Preparation of N-(4-Succinimidoxycarbonylbutyl)carbamazepine-Amine-Enriched HRP (Horseradish Peroxidase) Conjugate (Label A)

Amine-enriched HRP was prepared as follows. Briefly, dry HRP (horseradish peroxidase) is dissolved in 0.1M MES buffer, pH 5.5, to achieve a final concentration of $2.5\times10^{-6}$ mol (100 mg) in 10 mL of buffer (MES=2-(N-morpholino)ethane sulfonic acid). The protein concentration was determined by A403 measurement using the conversion factor A403 1 mg/mL=2.24. The HRP solution was combined with $1.5\times10^{-3}$ mol (275 mg) of L-lysine monohydrochloride dissolved in 10 mL of 0.1M MES buffer at pH 5.5. A solution of freshly prepared 1-ethyl-3-(3-dimethylaminopropyl)carbodiimide hydrochloride (EDC, $5\times10^{-4}$ mol, 960 mL) in MES buffer was added. The container was capped and mixed overnight at room temperature. The reaction was dialyzed against 0.02M MOPS buffer at pH 7.0 (3 L at 10° C.). The dialysis buffer was changed 3 X. MOPS=3 -(N-morpholino)propanesulfonic acid.

Prior to reaction, a sample of the amine-enriched HRP was exchanged from MOPS buffer into 0.1M EPPS buffer, pH 8.0, using Centricell Centrifugal Ultrafilter (30,000 nominal molecular weight limit). This sample was then diluted to 5.0 mL to produce a solution with a final concentration of 10.00 mg/mL ($2.5\times10^{-4}$M). EPPS is N-(2-hydroxyethyl)piperazine-N'-3-propanesulfonic acid.

One mL of the amine-enriched HRP solution was added to a small vial ($2.5\times10^{-4}$M). 500 µL of dimethylformamide, Aldrich 22,705–6, containing 10 mM 4'-hydroxyacetanilide (DMF 4'-HA) was added to the vial, vortexed, and placed in a 42° C. water bath.

Meanwhile, the requisite carbamazepine hapten analogue was dissolved in DMF 4'-HA to yield a 21.54 mg/mL solution ($5.0\times10^{-2}$M). 500 µL of this solution was added to the HRP/DMF 4'-HA solution dropwise while vortex mixing. The molar ratio of the carbamazepine/HRP was 100/1.

Incubation was performed at 42° C. for 1 hour with gentle shaking in a water bath. The sample was transferred to Spectrapor #2 dialysis tubing along with an additional 0.5 mL of DMF 4'-HA/0.1M EPPS (1:1) used to rinse the reaction container.

The reaction was dialyzed as follows:

a) 1 L DMF 4'-HA/0.1M EPPS, pH 8.0 (1:1), at 42° C. for 1 hour b) Dialysis condition a) was repeated 1 X c) 1.5 L 0.1M EPPS, pH 8.0, containing 0.1% bovine serum albumin (BSA) at 5° C., 2 hours d) 1.5 L 0.1M EPPS, pH 8.0, at 5° C., overnight e) 2.0 L 40 mM Tris-HCl, 150 mM NaCl, pH 7.5, for at least 8 hours f) Dialysis condition e) was repeated 1 X Tris-HCl is tris(hydroxymethyl)aminomethane hydrochloride. Following dialysis, 0.02% merthiolate was added as a preservative, and the label was stored refrigerated.

Example 2

N-[6-(4-Succinimidoxycarbonylbutyramido)hexyl]carbamazepine-Amine-Enriched HRP (Label B)

Amine-enriched HRP was prepared as described in Example 1. Prior to reaction, a sample of the amine-enriched HRP was exchanged from MOPS buffer into 0.1M EPPS buffer, pH 8.0, using Centricell Centrifugal Ultrafilter (30,000 nominal molecular weight limit). This sample was then diluted to 3.0 mL to produce a solution with a final concentration of 8.36 mg/mL ($2.08 \times 10^{-4}$M). EPPS is N-(2-hydroxyethyl)piperazine-N'-3-propanesulfonic acid.

To prepare Label B, one mL of amine-enriched HRP was added to a small vial ($1.85 \times 10^{-5}$M). 500 µL of dimethylformamide, Aldrich 22,705–6, containing 10 mM 4'-hydroxyacetanilide (DMF 4'-HA) was added to the vial, vortexed, and placed in a 42° C. water bath.

Meanwhile, the requiste carbamazepine drug hapten analogue was dissolved in DMF 4'-HA to yield a 22.72 mg/mL solution ($4.16 \times 10^{-2}$M). 500 µL of this solution was added to the HRP/DMF 4'-HA solution dropwise while vortex mixing. The molar ratio of the carbamazepine/HRP was 100/1.

Incubation was performed at 42° C. for 1 hour with gentle shaking in a water bath. The sample was transferred to Spectrapor #2 dialysis tubing along with an additional 1 mL of DMF 4'-HA/0.1M EPPS (1:1) used to rinse the reaction container.

The reaction was dialyzed and stored as described in Example 1.

Example 3

N-{4-[4-(3-Succinimidoxycarbonylpropionyl)piperazinocarbonyl]butyl}carbamazepine-amine-Enriched HRP (Label C); and N-{4-[3-(4-Succinimidoxycarbonylbutyramido)propylaminocarbonyl]butyl}carbamazepine-Amine-Enriched HRP (Label D)

Amine-enriched HRP was prepared as described in Example 1 and exchanged into 0.1M EPPS buffer, pH 8.0, using Diaflo Ultrafilters YM30 filters (30,000 molecular weight cutoff) in Amicon Stirred Ultrafiltration Cells. This sample was then diluted to 3.18 mL to produce a solution with a final concentration of 10.00 mg/mL ($2.5 \times 10^{-4}$M).

One mL of amine-enriched HRP was added to each of two small vials. 500 µL of dimethylformamide, Aldrich 22,705–6, was added to each vial, vortexed, and placed in a 42° C. water bath for at least 15 minutes.

Meanwhile, Succinimidoxycarbonylpropionyl)piperazinocarbonyl]butyl}carbamazepine was dissolved in DMF to yield a 30.05 mg/mL solution ($2.5 \times 10^{-2}$M). To prepare Label C, 500 µL of this solution was added to the HRP/DMF solution dropwise while vortex mixing. Label D was prepared in the same manner, however, the hapten drug analogue N-{4-[3-(4-Succinimidoxycarbonylbutyramido)propylaminocarbonyl]butyl}carbamazepine was dissolved in DMF to 30.15 mg/mL ($2.5 \times 10^{-2}$M). The carbamazepine/HRP ratio for both labels is 100/1.

Incubation was performed at 42° C. for 1 hour with gentle shaking in a water bath. The samples were transferred to Spectrapor #2 dialysis tubing along with an additional 1 mL of DMF/0.1M EPPS (1:1) used to rinse the reaction container.

Each reaction mixture was dialyzed as follows:

a) 1 L DMF/0.1M EPPS, pH 8.0 (1:1), at 42° C. for 1 hour b) Dialysis condition a) was repeated 1 X c) 2.0 L 0.1M EPPS, pH 8.0, containing 0.1% bovine serum albumin (BSA) at 8° C., overnight d) 2.0 L 0.02M MOPS, pH 7.0, at 8° C., 8 hours e) Dialysis condition d) was repeated 2 X, overnight and 8 hours Following dialysis, 0.02% merthiolate was added as a preservative, and the label was stored refrigerated.

Example 4

Preparation of Carbamazepine-Amine-Enriched HRP Labels E, F, and G

N-[6-(4-Succinimidoxycarbonylbutyramido)hexyl]carbamazepine-amine-enriched HRP (Label E);

N-{4-[4-(3-Succinimidoxycarbonylpropionyl)piperazinocarbonyl]butyl}carbamazepine-amine-enriched HRP (F); and N-{4-[3-(4-Succinimidoxycarbonylbutyramido)propylaminocarbonyl]butyl}carbamazepine-amine-enriched HRP (Label G)

Amine-enriched HRP was prepared as described in Example 1 and exchanged into 0.1M EPPS buffer, pH 8.0, to yield several mL of a 10.00 mg/mL solution ($2.48 \times 10^{-4}$M). Three labels were prepared with 1 mL of amine-enriched HRP each. 500 µL DMSO, was added dropwise with vortex mixing to each sample. The samples were preincubated at room temperature for at least 20 minutes with shaking at 2400 rpm.

Meanwhile, N-[6-(4-Succinimidoxycarbonylbutyramido)hexyl]carbamazepine was dissolved in DMSO to yield a 27.08 mg/mL solution ($2.48 \times 10^{-2}$M). Label E was made by adding 500 µL of this solution to one of the HRP/DMSO solutions prepared above. The hapten was added dropwise while vortex mixing. The Labels F and G were prepared as described above, but the hapten solutions were made as follows:

N-{4-[4-(3-Succinimidoxycarbonylpropionyl)piperazino-carbonyl]butyl}carbamazepine was dissolved to 29.81 mg/mL ($2.48 \times 10^{-2}$M) and used to make Label F; N-{4-[3-(4-Succinimidoxycarbonylbutyramido)propylaminocarbonyl]butyl}carbamazepine was dissolved to 29.91 mg/mL ($2.48 \times 10^{-2}$M) and used to make Label G. The molar ratio of all three labels was 100/1 carbamazepine to HRP.

Incubation was performed at room temperature for 4 hours with shaking at 2400 rpm. The samples were each transferred to Spectrapor #2 dialysis tubing along with an additional 1 mL of dialysate to rinse the reaction containers. The labels were dialyzed into 0.02M MOPS buffer, pH 7.0, at 5°–10° C. This dialysis condition was repeated 3 X with 2 to 3 L of buffer each time. Following dialysis, 0.02% merthiolate was added as a preservative, and the labels were stored refrigerated.

The invention has been described in detail with particular reference to preferred embodiments thereof, but it will be understood that variations and modifications can be effected within the spirit and scope of the invention.

What is claimed is:

1. A labeled carbamazepine analogue conforming to the structure (I):

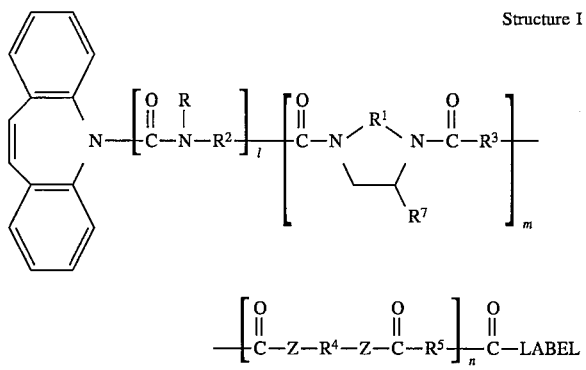

R represents hydrogen or lower alkyl of 1 to 6 carbon atoms $R^1$ is alkylene of 1 to 3 carbon atoms sufficient to form a heterocyclic group selected from 1,4-piperazinylene; 2,5-dimethyl-1,4-piperazinylene; 1,3-imidazolidinylene, and 1,4-hexahydrodiazepinylene;

$R^2$, $R^3$, $R^4$, and $R^5$ each independently represent alkylene groups of 2 to 10 carbon atoms, or phenylene;

$R^7$ is hydrogen or methyl;

each Z independently represents —O—, —S—, or —NR— wherein R represents hydrogen or lower alkyl of 1 to 6 carbon atoms:

LABEL is an enzyme;

l is 0, 1 or 2;

m is 1 or 2;

n is 0, 1, or 2; and (i) provided that the bracketed components l, m and n of structure I can appear therein in any order, and (ii) only one $R^2$, $R^3$, $R^4$, or $R^5$ group can be phenylene.

2. The analogue of claim 1 wherein the linking chain includes one or more 1,4-piperazinylene ring groups.

3. The analogue of claim 1 wherein the label is horseradish peroxidase or amine-enriched horseradish peroxidase.

4. The analogue of claim 1 according to structure I wherein:

$R^1$ represents ethylene thereby forming, with the atoms to which it is bonded, a 1,4-piperazinylene ring group;

$R^2$, $R^3$, $R^4$, and $R^5$ each independently, represent methylene, ethylene, trimethylene, tetramethylene, pentylene, or hexylene; and each Z independently represents —O— or —NH—, LABEL is horseradish peroxidase or amine-enriched horseradish peroxidase.

5. The labeled carbamazepine analogue of claim 4 which is a conjugate of amine enriched horseradish peroxidase and the carbamazepine analogue is N-{4-[4-(3 -Succinimidoxycarbonylpropionyl)piperazinocarbonyl]butyl}carbamazepine.

6. A labeled carbamazepine analogue wherein the label is amine enriched horseradish peroxidase and the carbamazepine analogue is selected from the group consisting of N-[6-(4 -Succinimidoxycarbonylbutyramido)hexyl]-carbamazepine; and N-{4-[3-(4-Succinimidoxycarbonylbutyramido)propylaminocarbonyl]butyl}carbamazepine.

7. A method for making labeled carbamazepine hapten analogues comprising the steps of:

A) contacting (i) a label having an amine or sulfhydryl group thereon, with an excess of a (ii) carbamazepine analogue comprising:

(a) a succinimidoxy group;

(b) a carbamazepine nucleus; and (c) a linking chain linking the carboxamide group of the carbamazepine nucleus to the succinimidoxy group through a carbonyl group; and B) removing the unused carbamazepine analogue and condensation by-products; wherein the label and the analogue are each separately dissolved in a water-miscible organic solvent selected from the group consisting of N,N-dimethylformamide, dimethyl sulfoxide and a buffered mixture of water and N,N-dimethylformamide or dimethyl sulfoxide before the label and the analogue are contacted with each other.

* * * * *